United States Patent
Houge et al.

(10) Patent No.: US 6,870,950 B2
(45) Date of Patent: Mar. 22, 2005

(54) METHOD FOR DETECTING DEFECTS IN A MATERIAL AND A SYSTEM FOR ACCOMPLISHING THE SAME

(75) Inventors: Erik C. Houge, Orlando, FL (US); Catherine Vartuli, Windermere, FL (US); Mike Antonell, Orlando, FL (US); Pam Cavanagh, Orlando, FL (US); Hui Ma, Gainesville, FL (US)

(73) Assignee: Agere Systems Inc., Allentown, PA (US)

( * ) Notice: Subject to any disclaimer, the term of this patent is extended or adjusted under 35 U.S.C. 154(b) by 637 days.

(21) Appl. No.: 09/809,379

(22) Filed: Mar. 15, 2001

(65) Prior Publication Data

US 2002/0131631 A1 Sep. 19, 2002

(51) Int. Cl.⁷ ................................................ G06K 9/00
(52) U.S. Cl. ..................................... 382/149; 356/237.1
(58) Field of Search ................................ 382/149, 145, 382/141; 356/237.1, 237.2, 237.5

(56) References Cited

U.S. PATENT DOCUMENTS

| | | | | |
|---|---|---|---|---|
| 5,406,213 A | * | 4/1995 | Henley | 324/753 |
| 5,808,735 A | * | 9/1998 | Lee et al. | 356/237.2 |
| 5,867,597 A | * | 2/1999 | Peairs et al. | 382/209 |
| 6,366,688 B1 | * | 4/2002 | Jun et al. | 382/145 |
| 6,535,621 B1 | * | 3/2003 | Fujita | 382/112 |

* cited by examiner

*Primary Examiner*—Bhavesh M. Mehta
*Assistant Examiner*—John Strege (57) ABSTRACT

The present invention provides a method for detecting defects in a material and a system for accomplishing the same. The method includes obtaining an image of at least a portion of a material's surface and converting the image into an intensity profile. The method further includes determining a defect in the material's surface from the intensity profile. In one exemplary embodiment, the image is an electron image obtained using a scanning electron microscope. The method may further be used to determine a defect density in the material's surface.

25 Claims, 7 Drawing Sheets

METHOD FOR DETECTING DEFECTS IN A MATERIAL AND A SYSTEM FOR ACCOMPLISHING THE SAME

TECHNICAL FIELD OF THE INVENTION

The present invention is directed, in general, to a method of testing and, more specifically, to a method for detecting defects in a material, and a system for accomplishing the same.

BACKGROUND OF THE INVENTION

Stainless steel pipes provide various functions in a multitude of technologies. One function stainless steel pipes currently provide is transporting corrosive fluid, or gases containing chlorine or fluorine etches used in the manufacture of semiconductor devices, from one point to another. Commonly, such corrosive fluids or gases adversely react with microdefects, such as pin holes, boundary junctions and triple points, causing corrosion and eventual rupture of the stainless steel pipe. For safety purposes, it is, therefore, desired to monitor the pin holes and other defects in the structure of the stainless steel pipe during use or as an incoming verification.

In an attempt to standardize the defect detection process and provide a safe work environment, an American Society for Testing and Materials (ASTM) standard for testing stainless steel pipe has been developed. Currently, the ASTM standard method employed to measure the quality of stainless steel pipe is accomplished by taking a microscopic picture at 3500 times magnification and then overlaying a 1 cm square grid on top of the picture. A human then counts the number of boxes in the grid that have defects, assigning a defect density to the stainless steel pipe.

The aforementioned ASTM standard is extensively used, unfortunately, it experiences certain drawbacks. First, the ASTM standard may not focus on a random point of the stainless steel pipe. Focusing the microscope requires that there be a point on which to focus. This requires, in general, that the focusing be done in areas where there is something to focus on, such as an area having a large amount of defects. Since the microscope is typically focused on a point having the highest number of defects, an inaccurate defect count may be obtained.

A second drawback of the ASTM standard stems from inaccuracies resulting from human error. One of such human error inaccuracies is caused by variations in counting style between various people. Where one person counting might record multiple defects in a single square as multiple defects, another person counting might record the multiple defects within the single square as a single defect. A similar situation might occur with a defect spanning multiple squares.

Another inaccuracy resulting from human error, stems from the limited area that may be tested using the human eye. The area that is seen with the microscope is very small with respect to the length and area of the stainless steel tubing. This only provides an average of the defects over an extremely small area, not a complete reading. In essence, the methodology of placing a square grid over a picture is better suited for making a course defect density, rather than for extremely precise measurements, as currently desired in the industry.

Accordingly, what is needed in the art is a method of testing the surface of a stainless steel pipe for defects that does not experience the drawbacks as experienced with the prior art methods.

SUMMARY OF THE INVENTION

To address the above-discussed deficiencies of the prior art, the present invention provides a method for detecting defects in a material, and a system for accomplishing the same. The method includes obtaining an image of at least a portion of a material's surface and converting the image into an intensity profile. The method further includes determining a defect in the material's surface from the intensity profile. In one exemplary embodiment, the image is an electron image obtained using a scanning electron microscope. The method may further be used to determine a defect density in the material's surface.

The present invention therefore introduces a method for detecting defects in a material that does not experience the uncertainties experienced in the prior art methods. Since defects in the material may be determined with more certainty, any safety or reliability issues associated with the material may be substantially reduced, saving valuable time and money.

The foregoing has outlined, rather broadly, preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
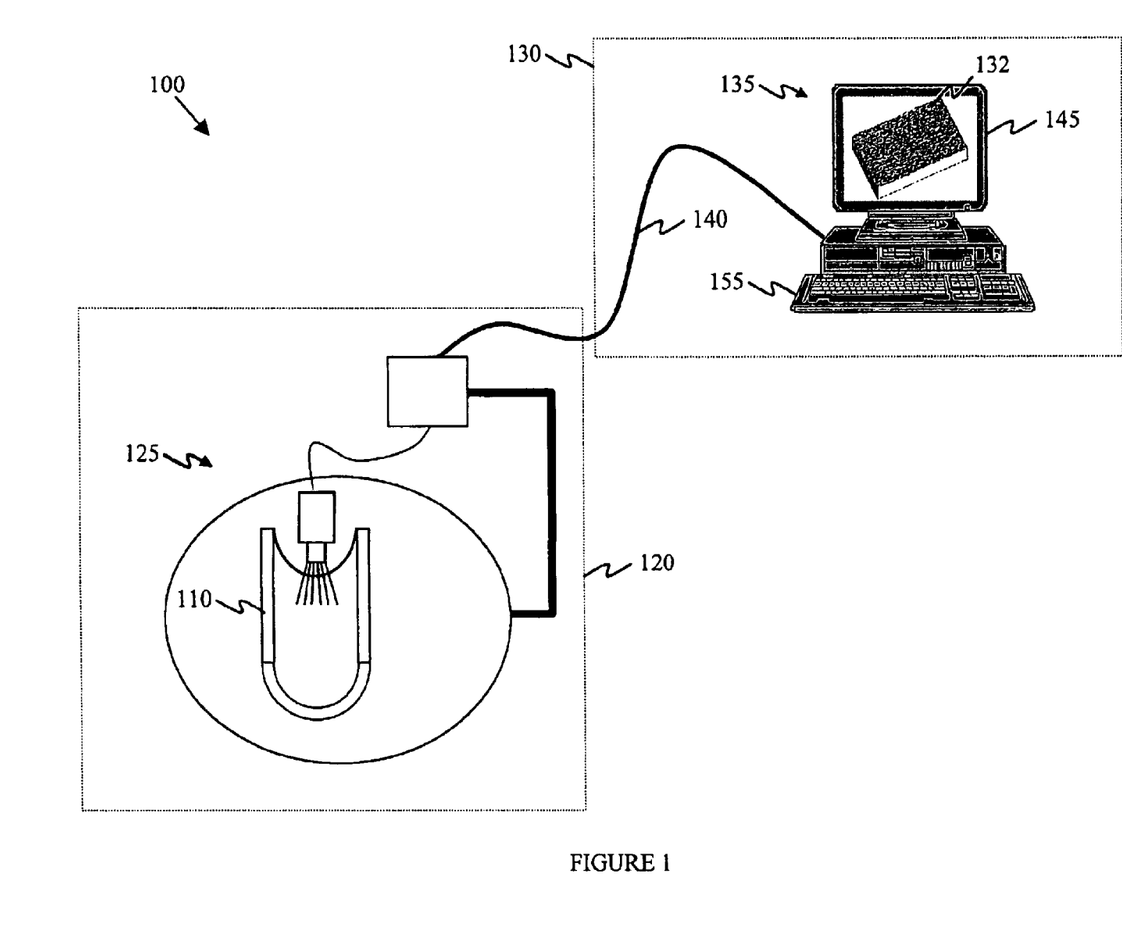
FIG. 1 illustrates a partial sectional view of an exemplary embodiment of a system for detecting defects in a material, which may be used in accordance with the principals of the present invention.

Referring initially to FIG. 1, illustrated is a partial sectional view of an exemplary embodiment of a system 100 for detecting defects in a material 110, which may be used in accordance with the principals of the present invention. It should initially be noted that the system 100 may include many objects, and is not limited by what is illustrated in the embodiment shown in FIG. 1.

In the embodiment shown in FIG. 1, the system 100 includes a first subsystem 120 and a second subsystem 130. The first subsystem 120, obtains an image of at least a portion of the material 110, which in an exemplary embodiment may be a conduit. In a preferred embodiment of the invention, the first subsystem 120 may include a scanning electron microscope (SEM) 125 that obtains an electron image of at least a portion of the material 110. It should be noted, however, that the first subsystem 120 may include other subsystems designed to detect defects in the material's 110 surface, including a transmission electron microscope (TEM), a scanning transmission electron microscope (STEM), optical microscope, auger electron spectroscopy (AES), or x-ray photoelectron spectroscopy (XPS).

As previously mentioned, the system 100 may further include a second subsystem 130. The second subsystem 130 converts the image into an intensity profile 132 and determines a defect in the material's 110 surface from the intensity profile 132. It should be noted that the second subsystem 130 may include any subsystem capable of accurately using information obtained from the first subsystem 120. In the embodiment illustrated in FIG. 1, the second subsystem 130 includes a computer subsystem 135. The computer subsystem 135 may be coupled to the first subsystem 120 via a cable 140, and may be configured to receive and process information from the first subsystem 120. In one embodiment of the present invention, the computer subsystem 135 may be software residing on a conventional personal computer. The software embodiment includes source code, object code, libraries, executable programs and other software structures that cooperatively function together to achieve the functionality of the present invention. The computer subsystem 135 may also include an operator interface, such as a monitor 145, a keyboard 155, or a printer (not shown). Alternatively, however, the monitor 145 and the keyboard 155 may be replaced by other conventional output and input devices, respectively.

It should be noted that any conventional computer system having at least one CPU that is suitable to function as the computer subsystem 135, including without limitation, hand-held units, laptop/notebooks, minis, mainframes and supercomputers, including RISC and parallel processing architectures, as well as combinations of such systems, may be used. Conventional computer system architecture is more fully discussed in *Computer Organization and Architecture*, by William Stallings, MacMillan Publishing Co. (3rd ed. 1993), which is also incorporated herein by reference. Alternative computer system embodiments may be firm-or hardware-based. It should also be noted that the second subsystem 130 is not limited to an external source and may be included within a logic provided in the first subsystem 120.

Figure 2:
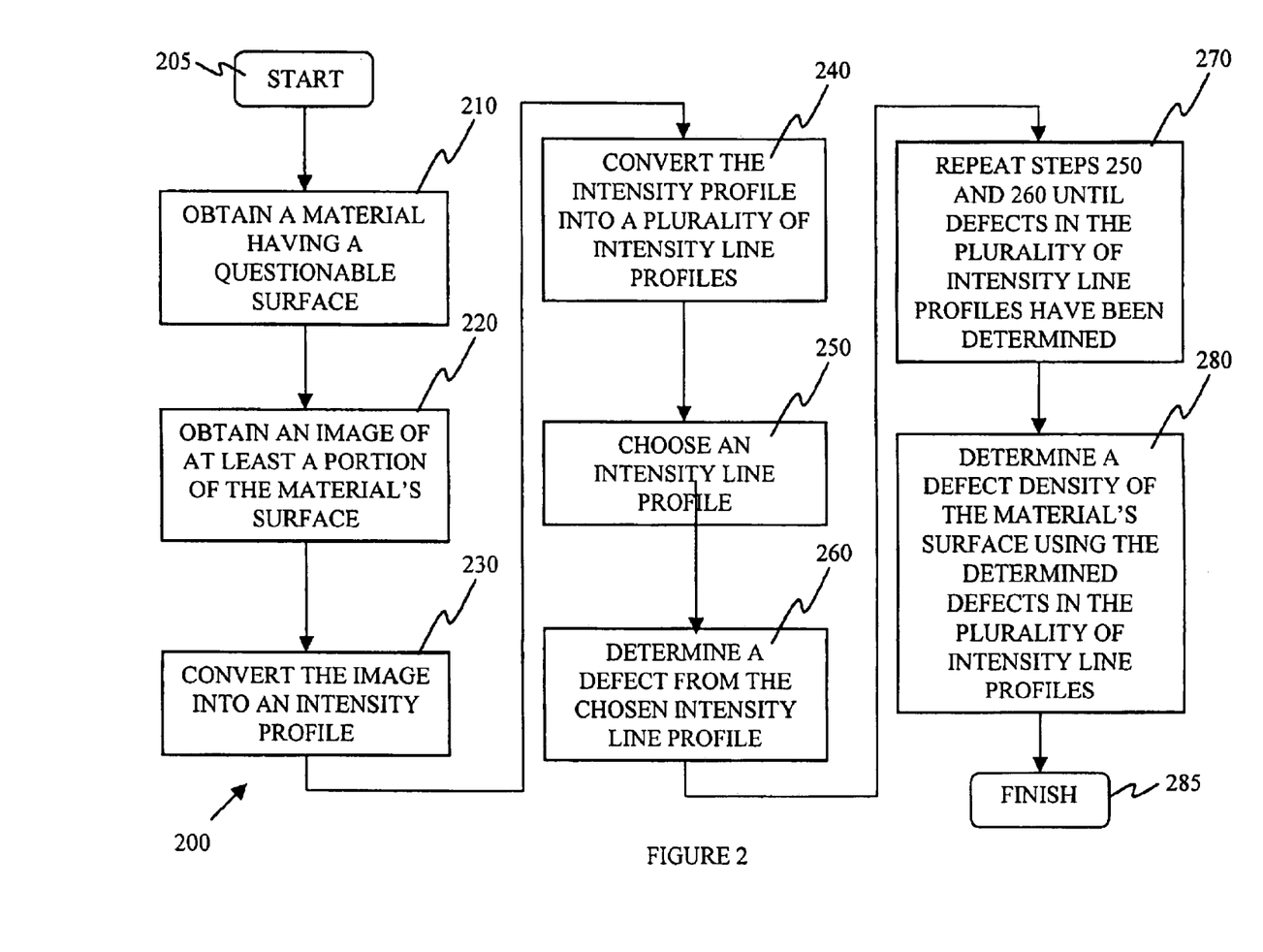
FIG. 2 illustrates a flow diagram of a method for detecting defects in a material, which may be used in accordance with the principals of the present invention.

Turning now to FIG. 2, with continued reference to FIG. 1, illustrated is a flow diagram 200 of a method for detecting defects in the material 110. In FIG. 2, the method begins in a step 205. In a step 210, the material 110, having a questionable surface, is obtained. The material 110 having a questionable surface may be obtained from a material that has already been used, or in an exemplary embodiment, may be attained from an unused material, as an incoming verification therefor. The material 110 may comprise any material wherein a defect is desired to be located, however, in an exemplary embodiment of the invention the material 110 is a metal conduit, such as a stainless steel tubing located in a semiconductor wafer manufacturing facility. As illustrated, the material 110 may be cross-sectioned to expose an inner surface of the material 110.

Figure 3:
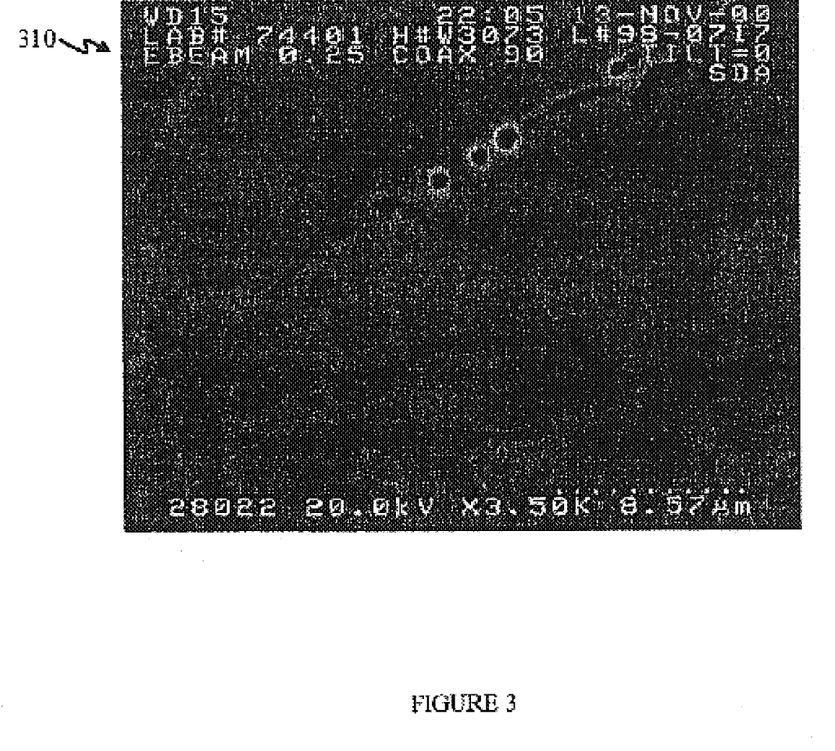
FIG. 3 illustrates a simulation of a 20 keV electron beam as it interacts with the material's surface, producing an image, such as an electron image.

Subsequent to obtaining the material 110, in a step 220, an image of at least a portion of the material's 110 surface should be obtained. To obtain an image of the material's 110 surface, the first subsystem 120 scans the surface of the material 110. In the preferred embodiment where the first subsystem 120 includes the SEM 125, the SEM 125 observes many points on the material's 110 surface to obtain an accurate electron image. In an alternative embodiment, the first subsystem 120 rasters across the material's 110 surface to obtain the image. Turning to FIG. 3, illustrated is an image 310 of a 20 keV electron beam as it interacts with the material's 110 surface.

Figure 4:
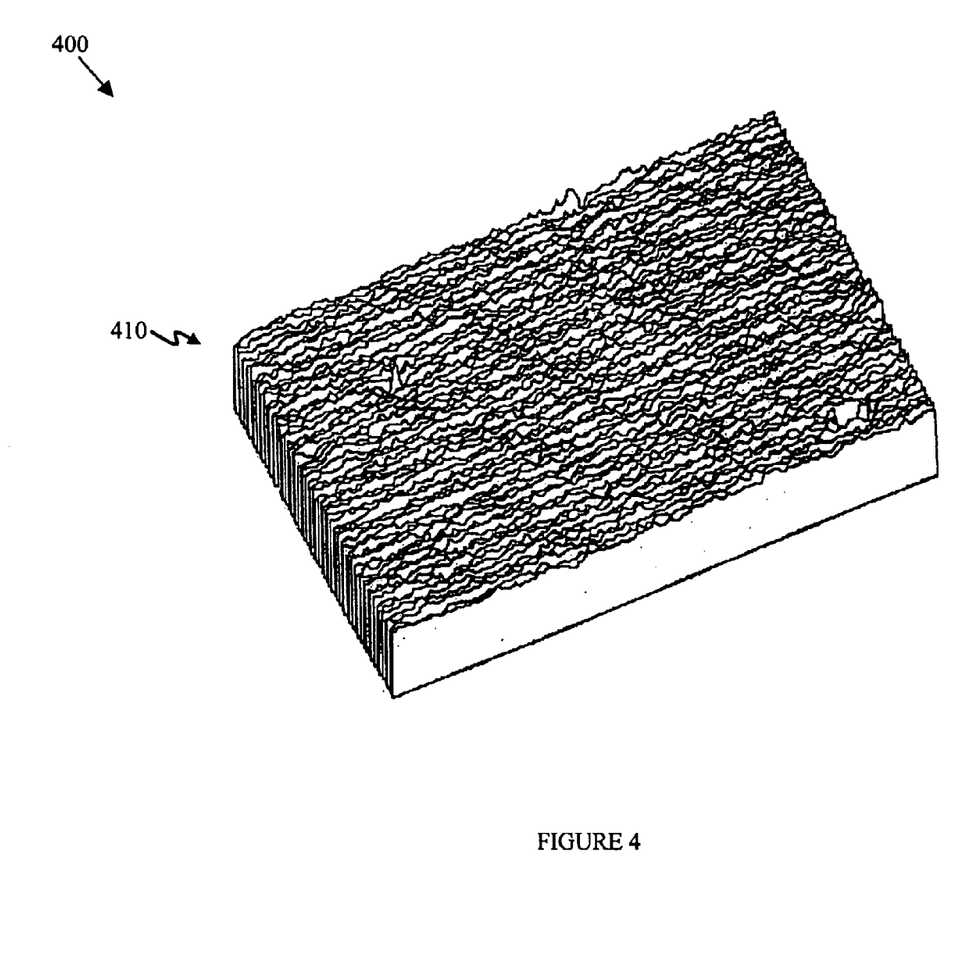
FIG. 4 illustrates an intensity profile in accordance with the principals of the present invention.

After obtaining the image 310 of at least a portion of the material's 110 surface, in a step 230, the second subsystem 130 coverts the image 310 into an intensity profile 410, such as illustrated in FIG. 4. The intensity profile 410 is essentially a three dimensional makeup of the material's 110 surface. The intensity profile 410 may further include a total number of intensity pixels, wherein each intensity pixel is assigned an intensity value. In an exemplary embodiment of the invention, a discrete 8 bit intensity value (256 possibilities) is assigned to each of the total number of intensity pixels. One skilled in the art understands, however, that the present invention is not limited to the discrete 8 bit scale, and that other classification scales are within the scope of the present invention.

In an optional step 240, the second subsystem 130 may convert the intensity profile 410 into a plurality of intensity line profiles, each containing intensity line pixels. Taken as individual line profiles, defects on the material's 110 surface may be easily discerned from the intensity profile 410. In a step 250, an initial intensity line profile is chosen.

Figure 5:
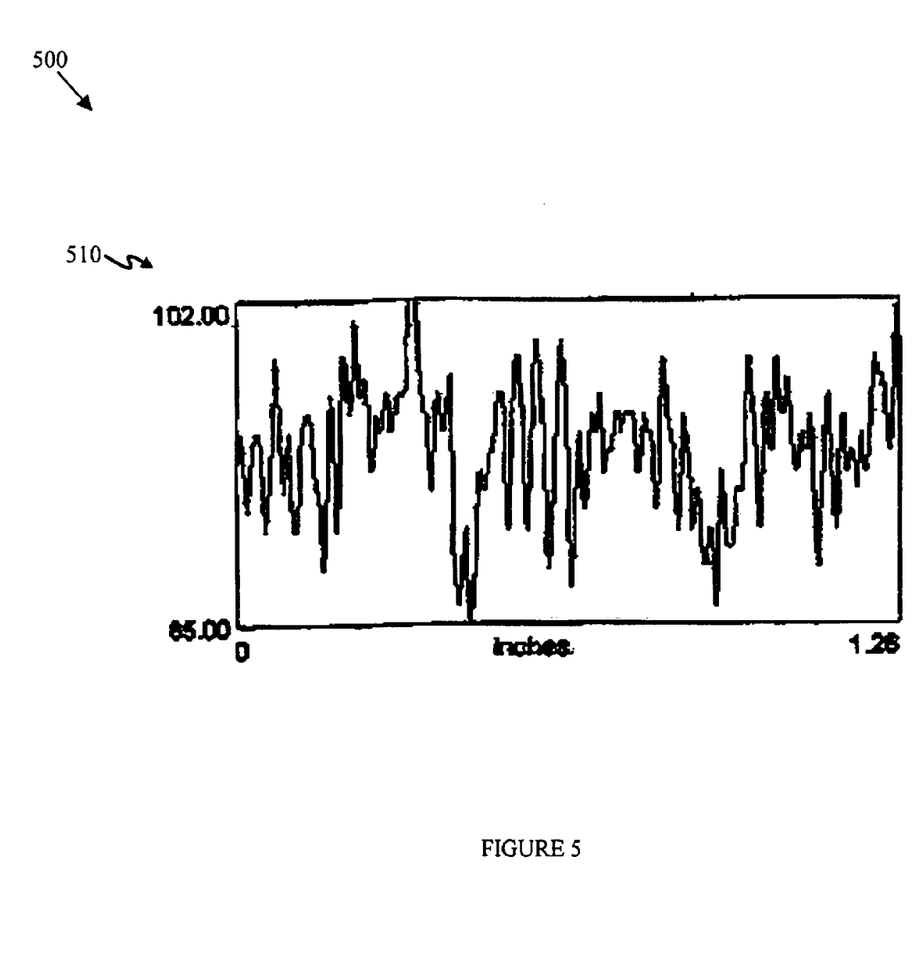
FIG. 5 illustrates an example of an initial intensity line profile in accordance with the principals of the present invention.

Turning to FIG. 5, illustrated is an example of an initial intensity line profile 500. In the present example shown in FIG. 5, the initial intensity line profile 500 depicts background intensity pixels. In an exemplary embodiment, the background intensity pixels may be determined by determining the average intensity value for the intensity line pixels of the initial intensity line profile 500, and plotting how far each intensity line pixel value varies from the average intensity value. The plot, in an exemplary embodiment, should plot as a histogram of intensity line pixels.

Figure 6:
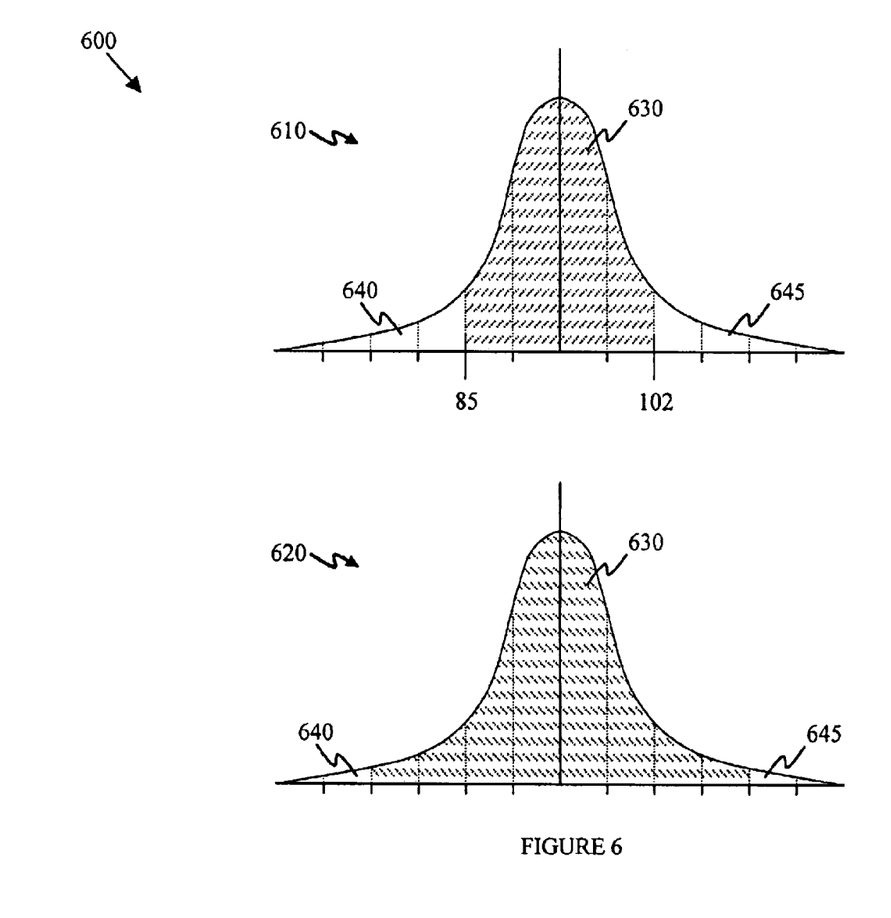
FIG. 6 illustrates two representative histograms representing a background area and defect areas, for 2 sigma and 4 sigma values, in accordance with the principals of the present invention.

In a step 260, in conjunction with conventional statistical analysis, a desired sigma value may be chosen, wherein any intensity line pixel within the desired sigma value is a background intensity pixel and any intensity line pixel outside the desired sigma value is a defect intensity pixel. In one particularly advantageous embodiment, the desired sigma value is about 2 sigma (approximately 66.67% confidence), however, in an alternative embodiment, the desired sigma value is 4 sigma (approximately 99.99% confidence). Turning briefly to FIG. 6, illustrated are two representative histograms 610, 620, representing a background area 630 and defect areas 640, 645, for the 2 sigma and 4 sigma values, respectively.

Referring back to FIG. 5, the average intensity value of the intensity line profile 500 is approximately 92 and the standard deviation is about 4.62. Using the 2 sigma evaluation as illustrated in FIG. 5, all intensity line pixel values between about 102 and about 85 are considered background intensity pixel values. Any pixel having an intensity line pixel value less than about 85 or greater than about 102 can be considered a defect pixel. In an exemplary embodiment of the present invention, intensity line pixel values greater than about 102 are considered positive defects, or deposits, on the material's 110 surface, and intensity line pixel values less than about 85 are considered negative defects, or pinholes, in the material's 110 surface. In accordance with one embodiment of the present invention, negative defects, e.g., pinholes, boundary junctions or triple points, are the only defects of concern, since positive defects do not have an effect of the safety of the material 110. In such a situation, any pixel with a value over about 85 would be considered a background pixel. Referring briefly back to FIG. 6, the only defect area of concern would be the defect area 640, since the defect area 645 would not substantially affect the safety of the material 110. It should be noted, however, this is not always the case, and that positive defects may cause contamination and thus breakthrough of a protective oxide layer on an inner surface of the material 110, causing harm.

Figure 7:
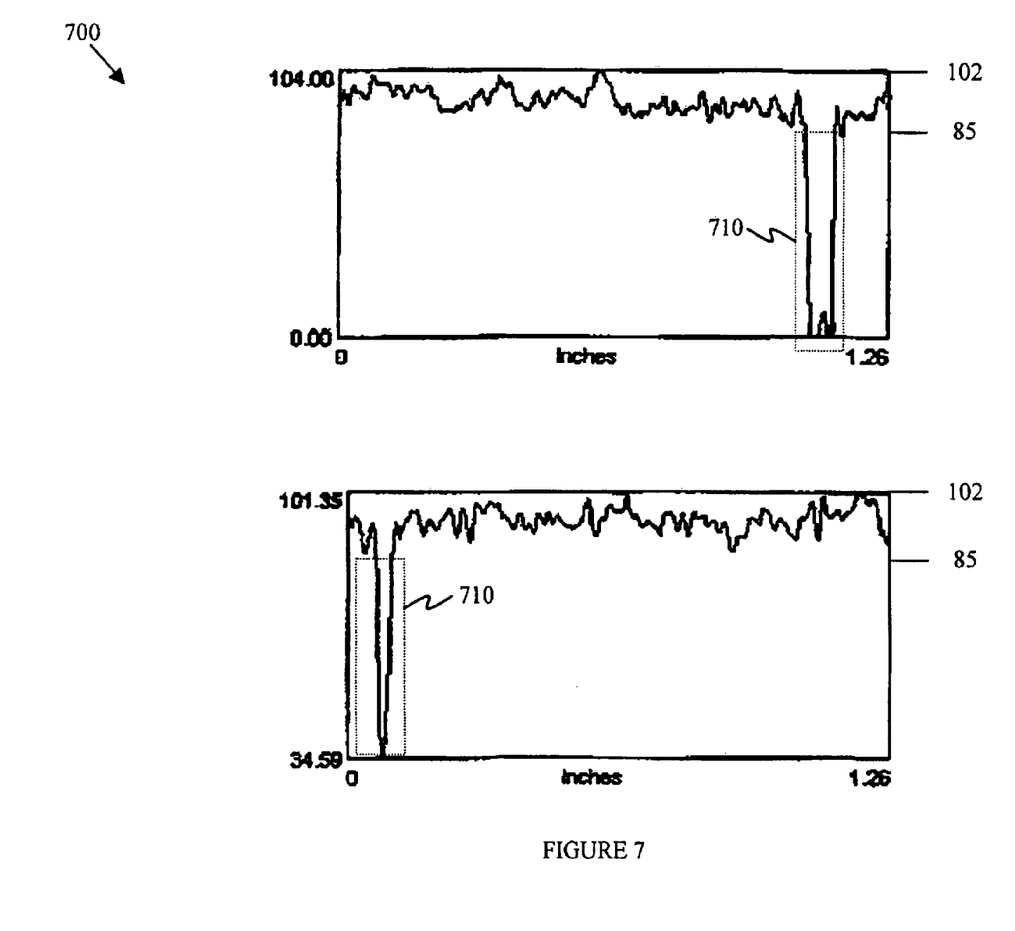
FIG. 7 illustrates an example of an intensity line profile having defect pixels therein, in accordance with the principals of the present invention.

Turning to FIG. 7, illustrated is an example of an intensity line profile 700 having defect pixels 710 therein. As illustrated, the defect pixels 710 are a drastic variation from the background intensity pixel range, which in the present example ranges from about 85 to about 102. In the given example illustrated in FIG. 7, out of about 63,488 total intensity line pixels, the number of defect pixels is about 204 pixels.

In a step 270, after determining the number of defect pixels within the initial intensity line profile 500, steps 250 and 260 may be repeated for the remainder of the plurality of intensity line profiles. From the total number of defect pixels, out of a total number of intensity pixels within the intensity profile, in a step 280, a defect density may be calculated. The defect density, may be calculated by dividing the total number of defect intensity pixels by the total number of intensity pixels. If the value is greater than a predetermined percentage, the material 110 may be labeled defective and discarded, however, if it is lower than the predetermined percentage, the material 110 may be installed, or continue to be used, with a substantial assurance of the quality of the material 110. After determining the defect density, the process would subsequently finish in a step 285, preferably after scanning a large enough area of the material 110 to provide statistical relevance. It should be noted that the present method could determine a defect density of the material 110 directly from the intensity profile 410, without individually testing the plurality of intensity line profiles 500.

In one advantageous embodiment of the present invention, the system 100 may be used for detecting defects in the material 110, wherein the material 110 is a subset of a batch of the material. In such a situation, the batch of the material could be rejected based upon a number of defects detected in the material's 110 surface, saving the requirement of testing each material 110 in the batch.

The above-mentioned method of testing materials for defects is far more effective, and removes much of the variability that currently exists using the prior art method. Moreover, the automated way of verifying the quality of the material will increase the assurance that substantially no leaks exist in materials carrying hazardous materials, such as the conduit previously described.

Although the present invention has been described in detail, those skilled in the art should understand that they can make various changes, substitutions and alterations herein without departing from the spirit and scope of the invention in its broadest form.

What is claimed is:

1. A method for detecting defects in a material, comprising:
    obtaining an image of at least a portion of a material's surface;
    converting the image into an intensity profile;
    selecting an intensity line profile from the intensity profile;
    counting a number of defect intensity pixels from the intensity line profile; and
    determining a defect density in the material's surface from the intensity line profile of the intensity profile.

2. The method as recited in claim 1 wherein obtaining an image includes obtaining an electron image.

3. The method as recited in claim 2 wherein obtaining an electron image includes obtaining an electron image using a scanning electron microscope.

4. The method as recited in claim 1 further including selecting a plurality of intensity line profiles from the intensity profile and counting a number of defect intensity pixels from the plurality of intensity line profiles, and further determining the defect density in the material's surface from the plurality of intensity line profiles of the intensity profile.

5. The method an recited in claim 1 wherein determining a defect density of the material's surface includes determining a total number of intensity pixels.

6. The method as recited in claim 5 wherein determining a total number of intensity pixels includes determining number of background intensity pixels and a number of defect intensity pixels.

7. The method as recited in claim 6 wherein determining a defect density includes dividing the number of defect intensity pixels by the total number of intensity pixels.

8. The method as recited in claim 6 wherein the total number of intensity pixels comprise a histogram and the background intensity pixels are inside a desired sigma value and the defect intensity pixels are outside the desired sigma value.

9. The method as recited in claim 8 wherein the desired sigma value is greater than about 2 sigma.

10. The method as recited in claim 9 wherein the desired sigma value is greater than about 4 sigma.

11. The method as recited in claim 7 wherein the intensity profile includes a plurality of pixels and determining a defect of the material's surface further includes determining an average intensity of the plurality of pixels or determining a standard deviation of the intensity profile.

12. The method as recited in claim 7 wherein the number of defect intensity pixels does not include the number of defect intensity pixels having an intensity greater than an average intensity.

13. The method as recited in claim 1 wherein obtaining an image of at least a portion of a material's surface includes obtaining an image of an inner surface of a tubing located in a semiconductor wafer manufacturing facility.

14. A system for detecting defects in a material, comprising:
    a first subsystem that obtains an image of at least a portion of a material's surface; and
    a second subsystem that converts the image into an intensity profile, selects an intensity line profile from the intensity profile, counts a number of defect intensity pixels from the intensity line profile, and determines a defect density in the material's surface from the intensity line profile of the intensity profile.

15. The system as recited in claim 14 wherein the first subsystem includes a scanning electron microscope that obtains an electron image.

16. The system as recited in claim 14 wherein the second subsystem includes a computer subsystem including an operator interface.

17. The system as recited in claim 14 wherein the second subsystem determines a total number of intensity pixels.

18. The system as recited in claim 17 wherein the total number of intensity pixels includes a number of background intensity pixels and a number of defect intensity pixels.

19. The system as recited in claim 18 wherein determining a defect density includes dividing the number of defect intensity pixels by the total number of intensity pixels.

20. The system as recited in claim 18 wherein the total number of intensity pixels comprise a histogram and the background intensity pixels are inside a desired sigma value and the defect intensity pixels are outside the desired sigma value.

21. The system as recited in claim 20 wherein the desired sigma value is greater than about 2 sigma.

22. The system as recited in claim 21 wherein the desired sigma value is greater than about 4 sigma.

23. The system as recited in claim 14 wherein the material is a tubing located in a semiconductor wafer manufacturing facility.

24. A method of using a system for detecting defects in a material, comprising:
   detecting defects in a material, including;
      obtaining an image of the materials surface;
      converting the image into an intensity profile;
      selecting an intensity line profile from the intensity profile;
      counting a number of defect intensity pixels from the intensity line profile; and
      determining defects in the material's surface from the intensity line profile of the intensity profile; and
   rejecting the material based upon a number of the defects in the material's surface.

25. The method as recited in claim 24 wherein the material is a subset of a batch of the material and rejecting includes rejecting the batch of the material.

* * * * *